United States Patent [19]
Robertson et al.

[11] Patent Number: 5,677,335
[45] Date of Patent: Oct. 14, 1997

[54] 5-METHYL-ISOXAZOLE-4-CARBOXYLIC ACID ANILIDES AND 2-HYDROXYETHYLIDENE-CYANO ACETIC ACID ANILIDES FOR THE TREATMENT OF OCULAR DISEASE

[75] Inventors: Stella M. Robertson, Arlington; Laura Smith Lang, Bedford, both of Tex.

[73] Assignee: Alcon Laboratories, Inc., Fort Worth, Tex.

[21] Appl. No.: 674,368

[22] Filed: Jul. 2, 1996

Related U.S. Application Data

[62] Division of Ser. No. 317,276, Oct. 4, 1994, Pat. No. 5,583,150, which is a continuation of Ser. No. 835,243, Feb. 12, 1992, abandoned, which is a continuation of Ser. No. 569,671, Aug. 17, 1990, abandoned, which is a continuation-in-part of Ser. No. 395,860, Aug. 18, 1989, abandoned.

[51] Int. Cl.$^6$ ............................................. A61K 31/275
[52] U.S. Cl. .................................... 514/521; 514/912
[58] Field of Search ........................... 514/521, 912

[56] References Cited

U.S. PATENT DOCUMENTS

| | | | |
|---|---|---|---|
| 4,061,767 | 12/1977 | Ertel et al. | 424/282 |
| 4,087,535 | 5/1978 | Heubach | 424/272 |
| 4,284,786 | 8/1981 | Kammerer et al. | 548/248 |
| 4,351,841 | 9/1982 | Kammerer et al. | 424/272 |
| 5,459,163 | 10/1995 | Bartlett et al. | 514/521 |

FOREIGN PATENT DOCUMENTS

| | | |
|---|---|---|
| 0 013 376 | 7/1980 | European Pat. Off. . |
| 0 217 206 | 4/1987 | European Pat. Off. . |
| 0 257 882 | 3/1988 | European Pat. Off. . |
| 2 313 031 | 12/1976 | France . |
| 2 313 052 | 12/1976 | France . |

OTHER PUBLICATIONS

Nussenblatt et al., "Cyclosporine: Imunology Pharmacology and Therapuetic Uses," *Survey of Ophthalmology*, vol. 31(3), pp. 159–169, (1986).

BenEzra et al., "Cyclosporine Eyedrops for the Treatment of Severe Vernal Keratoconjunctivitis," *American Journal of Ophthalmology*, vol. 101, pp. 278–282, (1986).

Bartlett, et al., "Development of Autoimmunity in MRL/lpr Mice and the Effects of Drugs on this Murine Disease," *Scand. J. Rheumatology*, Suppl. 75, pp. 290–299, (1988).

Berkow, et al., "Allergic Conjunctivitis," and Vernal Keratoconjunctivitis, *The Merck Manual*, pp. 312 and 2222–2223, (1987).

Bartlett, "Immunopharmacological Profile of HWA 486, a Novel Isoxazol Derivative," *Int. J. Immunopharmacol.*, vol. 8, No. 2, pp. 199–204, (1986).

*Primary Examiner*—Zohreh Fay
*Attorney, Agent, or Firm*—Sally Yeager

[57] ABSTRACT

The use of 5-methyl-isoxazole-4-carboxylic acid anilides and 2-hydroxyethylidene-cyano acetic acid anilides for treating ocular diseases with immune etiology is disclosed.

8 Claims, No Drawings

5-METHYL-ISOXAZOLE-4-CARBOXYLIC ACID ANILIDES AND 2-HYDROXYETHYLIDENE-CYANO ACETIC ACID ANILIDES FOR THE TREATMENT OF OCULAR DISEASE

This is a divisional of U.S. patent application Ser. No. 08/317,276 filed Oct. 4, 1994 (allowed, but not yet issued now U.S. Pat. No. 5,583,150; which is a continuation of U.S. patent application Ser. No. 07/835,243 filed Feb. 12, 1992 (abandoned); which is a continuation of U.S. patent application Ser. No. 07/569,671 filed Aug. 17, 1990 (abandoned), which is a continuation-in-part of U.S. patent application Ser. No. 395,860, filed Aug. 18, 1989.

BACKGROUND OF THE INVENTION

This invention relates to the use of certain 5-methyl-isoxazole-4-carboxylic acid anilides and 2-hydroxyethylidene-cyano acetic acid anilides in treating ocular diseases with immune etiology. The compounds are also useful to prolong graft survival of corneal or other ocular tissues and as surgical adjuncts in patients who are atopic or immune impaired.

The 5-methyl-isoxazole-4-carboxylic acid anilides are generically disclosed in U.S. Pat. No. 4,087,535, which patent is fully incorporated herein by reference to the extent it defines the 5-methyl-isoxazole-4-carboxylic acid anilides and their synthesis. The compound, 5-methylisoxazole-4-carboxylic acid-4-trifluoromethyl-anilide (leflunomide) which is encompassed within the generic class, is specifically disclosed in U.S. Pat. Nos. 4,284,786 and 4,351,841. The metabolite of leflunomide and the metabolite's derivatives are described in U.S. Pat. No. 4,061,767 which is fully incorporated herein by reference to the extent it defines these compounds, which are 2-hydroxyethylidene-cyano acetic acid anilides, and their synthesis. Leflunomide's use as an antirheumatic, antiphlogistic, antipyretic, analgesic and as a compound for combating multiple sclerosis is also disclosed. In U.S. patent application Ser. No. 911,328 (now U.S. Pat. No. 5,459,163), leflunomide and its metabolite, herein referred to as AL 3318, are disclosed for combatting chronic graft-versus-host and autoimmune diseases. Ocular indications and topical administration is not discussed.

Steroids and antimetabolite compounds, such as cyclophosphamide, have been used orally to treat severe uveitis, such as that associated with Behcet's disease. Oral steroid therapy is usually accompanied by the topical use of steroid therapy (ocular) to more rapidly control the inflammation. Steroids are also used in conjunction with antiviral, antiparasitic or antifungal agents to treat uveitis associated with microbial infections. Both antimetabolite and steroid therapies are general immunosuppressive treatments with ocular and systemic side effects.

Cyclosporin A (CsA), a fungal-derived immunosuppressive agent, has recently been used to treat dry eye (in dogs), severe uveitis, vernal conjunctivitis and to prevent corneal graft rejection in humans; see, for example, Nussenblatt et al., *Survey of Ophthalmology*, Vol.31, No.3 (November–December 1986); and BenEzra et al., *American Journal of Ophthalmology*, Vol.101, p.298 (March 1986). CsA is effective, but has major side effects, including kidney damage and predilection for tumor formation. This makes long term therapeutic use, which is usually necessary, deleterious. In addition, due to its size and structure, CsA is not water soluble and currently must be delivered in a suitable lipophilic formulation which is not optimal for topical ophthalmic use.

SUMMARY OF THE INVENTION

The present invention is directed to methods for treating ocular diseases with immune etiology through the use of 5-methyl-isoxazole-4-carboxylic acid anilides and hydroxyethylidene-cyano acetic acid anilide derivatives. In addition the compounds are useful for treating ocular manifestations associated with systemic diseases with immune etiology. The compounds exhibit immunosuppressive, antiinflammatory, and mild antiallergic activity and are useful for the treatment of eye diseases such as uveitis (including rheumatoid nodules), retinitis, allergy (vernal keratoconjunctivitis and allergic or giant papillary conjunctivitis) and dry eye (Sjogren's syndrome). Additionally the compounds are useful for prolonging graft survival of corneal or other ocular tissue and are useful as surgical adjuncts in patients which are atopic or immune impaired.

The compounds are not universally cytotoxic, thereby overcoming the antimetabolite toxicity problems associated with the use of, for example, cyclophosphamide. In addition, the problems associated with the long term use of steroids are not encountered. The compounds of the present invention offer an alternative to cyclosporin and the complications associated with its long term use.

The compounds can be used for the treatment of ocular diseases and ocular manifestations associated with systemic diseases with immune etiology via oral, intravenous, intramuscular, topical and/or intraocular administration.

DETAILED DESCRIPTION OF PREFERRED EMBODIMENTS

The present invention relates to the treatment of ocular diseases through the the administration of compounds with the following formulas:

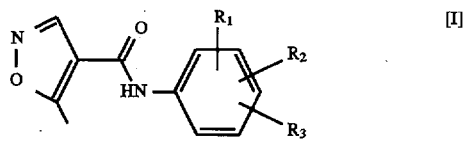

in which $R_1$, $R_2$ and $R_3$, which may be identical or different, each stand for an alkyl group of 1,2 or 3 carbon atoms, an alkoxy group of 1,2 or 3 carbon atoms, an alkylthio group of 1,2 or 3 carbon atoms, which groups may be substituted partly or totally by identical or different halogen atoms, such as fluorine, chlorine, bromine or iodine atoms;

halogen atoms, such as fluorine, chlorine, bromine or iodine;

nitro;

cyano;

alkoxycarbonyl groups of 1,2 or 3 carbon atoms in the alkyl moiety, and in which $R_1$ and $R_2$ each further stands for hydrogen, in which case, however, $R_3$ cannot stand for methyl but additionally can stand for a phenyl group which may carry one or two fluorine, chlorine, bromine or iodine atoms, alkyl groups of 1,2 or 3 carbon atoms or alkoxy groups of 1,2 or 3 carbon atoms, or for a phenoxy group which may carry one or two fluorine, chlorine, bromine or iodine atoms, alkyl groups of 1,2 or 3 carbon atoms or alkyoxy groups of 1,2 or 3 carbon atoms, or in which $R_1$ stands for hydrogen, and $R_2$ and $R_3$ together stand for a methylene-dioxy group or together with the phenyl ring, to which they are linked, they stand for a naphthalene ring; and

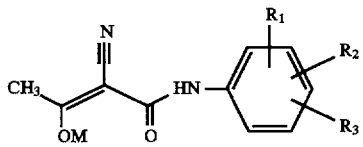

in which $R^1$, $R^2$ and $R^3$, which may be identical or different, each stands for an alkyl group of 1, 2, 3 or 4 carbon atoms, an alkoxy group of 1, 2 or 3 carbon atoms, an alkylthio group of 1, 2 or 3 carbon atoms, which groups may be substituted entirely or partly by identical or different halogen atoms, such as fluorine, chlorine, bromine or iodine; for a nitro, cyano or alkoxycarbonyl group of 1, 2 or 3 carbon atoms in the alkyl moiety; $R^1$ and $R^2$ each further stands for hydrogen, in which case, however, $R^3$ cannot stand for methyl but additionally stands for a phenyl group which may carry one or two fluorine, chlorine, bromine or iodine atoms, alkyl groups of 1, 2 3 or 4 carbon atoms, or alkoxy groups of 1, 2 or 3 carbon atoms, or for a phenoxy group which may carry one or two fluorine, chlorine, bromine or iodine atoms, alkyl groups of 1, 2 or 3 carbon atoms or alkoxy groups of 1, 2 or 3 carbon atoms, or $R^1$ stands for hydrogen, and $R^2$ and $R^3$ together stand for a methylene-dioxy group, or together with the phenyl ring, to which they are linked, they stand for a naphthalene ring, and in which M stands for hydrogen, an alkali metal, such as sodium or potassium, or ammonium.

The compounds described in [I] and [II] above exhibit antiallergic, antiinflammatory and/or immunomodulating activity. Because it is believed that the compounds are not general or broad spectrum immunosuppressants, such as antimetabolites and steroids, and because it is believed the compounds suppress T and B cell functions differently than CsA, the compounds of the present invention offer an alternative method for the treatment of ocular diseases and ocular manifestations of systemic diseases with immune etiology, collectively referred to herein as "ocular diseases".

The compounds represented by I and II above may be administered orally, intravenously, intramuscularly, topically and/or intraocularly for the treatment of ocular diseases. The compounds may be formulated as tablets, solutions or suspensions. The dose may vary from about 0.0001 mg/kg/day to about 30 mg/kg/day. Topical or intraocular delivery can include the use of ointments, liposomes, microspheres, palmitic-acid attachment or other lipid-like molecules useful in enhancing delivery to the eye. Oil or oil-like vehicles may also be used, however, an aqueous based vehicle is preferred.

The preferred compounds of the present invention have the following structures:

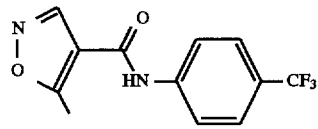

N-(4-Trifluoro-methylphenyl)-5-methylisoxazole-4-carboxamide (Leflunomide)

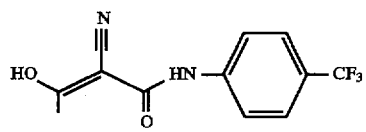

N-(4-trifluoromethylphenyl)-2-cyano-3-hydroxycrotonamide (AL 3318)

or their alkali metal or ammonium salt.

For the treatment of uveitis, dry eye and conjunctivitis leflunomide or AL 3318 can be administered systemically at a concentration of about 0.01–10 mg/kg/day or topically four times daily at a concentration of about 0.05–10 percent by weight (wt. %).

For the prevention of corneal graft rejection leflunomide or AL 3318 can be administered topically at about 0.05–20 wt. %; or systemically at about 0.01–30 mg/kg/day.

The following Examples illustrate formulations of the compounds of the present invention useful for the topical treatment of ocular diseases, particularly uveitis. They are in no way limiting.

EXAMPLE 1

Suspension

| Ingredient | Concentrations (wt. %) |
|---|---|
| Hydroxypropyl methylcellulose (HPMC) | 0.5 |
| Na2HPO4 | 0.2 |
| NaCl | 0.8 |
| EDTA | 0.01 |
| Benzalkonium chloride (BAC) | 0.01 |
| Tween 80 | 0.05 |
| Purified water | q.s. volume |
| pH | 7.4 |
| Osmolality | 290 mOsm/kg |
| Leflunomide | 1.0 + 2% xs |

Procedure 10 ml of the above suspension was made by first making the vehicle. This was done by adding, and quickly stirring, 2.508 g of HPMC in 250 ml of water at 90°–100° C. The composition was cooled to 5° C. with stirring. 1.013 g Na₂HPO₄, 4.002 g NaCl, 0.0535 g EDTA, 5.002 g BAC, 0.2569 g Tween were dissolved in about 200 ml of water, filtered through a corning 0.2 um filter unit and then added to the HPMC composition. The resulting mixture was brought to 500 ml with water. A suspension of leflunomide was then prepared by ball milling 0.1006 g leflunomide and 10 ml of the mixture made above with about 3 g of glass beads for 2 hours. The final suspension was then brought to volume with the mixture made above.

EXAMPLE 2

Aqueous

| Ingredient | Concentration (wt. %) |
|---|---|
| Na2HPO4 | 0.2 |
| NaCl | 0.8 |
| EDTA | 0.01 |
| BAC | 0.01 |
| Tween 80 | 0.05 |
| Purified water | q.s. |

| Ingredient | Concentration (wt. %) |
|---|---|
| pH | 7.42 |
| Osmolality | 291 mOsm/kg |
| Leflunomide | 1.0 |

Preparation

The above formulation can be made according to procedures known to those skilled in the art of making pharmaceutical preparations.

EXAMPLE 3

Ointment

| Ingredient | Concentration (wt. %) |
|---|---|
| Leflunomide | 1.0 |
| Methyl paraben | 0.05 |
| Propyl paraben | 0.01 |
| Anhydrous liquid lanolin | 4.0 |
| Mineral oil | 15.0 |
| White petrolatum | 79.94 |

Procedure

The above formulation can be made according to procedures known to those skilled in the art of making pharmaceutical preparations.

EXAMPLE 4

Suspension

| Ingredient | Concentration (wt. %) |
|---|---|
| Leflunomide | 0.5 + 2% xs |
| Carbopol 934P | 0.5 |
| Sodium chloride, USP | 0.4 |
| Mannitol, USP | 2.0 |
| Polysorbate 80, NF | 0.25 |
| Benzalkonium Chloride, NF | 0.01 + 5% xs |
| Disodium Edetate, USP | 0.01 |
| Hydrochloric acid, NF and/or sodium hydroxide, NF | |
| pH | 7.2 |
| Water for injection, USP | q.s. volume |

Procedure

The above suspension was prepared by first making the vehicle. The 500 ml of vehicle was prepared by adding to a 600 ml beaker, 10.0095 g of mannitol, 2.0002 g of NaCl, 0.0578 g EDTA and 2.510 g of carbopol to 400 g of water and stirring until homogenous. The pH was adjusted to $7^{+0.1}$ with NaOH. In a 50 ml beaker 0.1018 g BAC, and 1.2616 g Tween were added to about 30 ml of water and stirred, and added to the carbopol mixture, and water added to 500 g. A separate suspension of 0.1277 g leflunomide and 25.14 g of the above described vehicle was made. 20 g of that suspension and log of 4 mm glass beads were stirred for 2 days.

We claim:

1. A method for treating uveitis, which comprises:
administering a therapeutically effective amount of a compound with the formula:

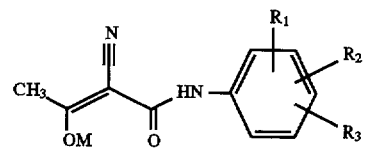

in which $R^1$, $R^2$ and $R^3$, which may be identical or different, each stands for an alkyl group of 1, 2, 3 or 4 carbon atoms, an alkoxy group of 1, 2 or 3 carbon atoms, an alkylthio group of 1, 2 or 3 carbon atoms, which groups may be substituted entirely or partly by identical or different halogen atoms, such as fluorine, chlorine, bromine or iodine; for a nitro, cyano or alkoxycarbonyl group of 1, 2 or 3 carbon atoms in the alkyl moiety; $R^1$ and $R^2$ each further stands for hydrogen, in which case, however, $R^3$ cannot stand for methyl but additionally stands for a phenyl group which may carry one or two fluorine, chlorine, bromine or iodine atoms, alkyl groups of 1, 2 3 or 4 carbon atoms, or alkoxy groups of 1, 2 or 3 carbon atoms, or for a phenoxy group which may carry one or two fluorine, chlorine, bromine or iodine atoms, alkyl groups of 1, 2 or 3 carbon atoms or alkoxy groups of 1, 2 or 3 carbon atoms, or $R^1$ stands for hydrogen, and $R^2$ and $R^3$ together stand for a methylene-dioxy group, or together with the phenyl ring, to which they are linked, they stand for a naphthalene ring, and in which M stands for hydrogen, an alkali metal, such as sodium or potassium, or ammonium.

2. The method of claim 1 wherein the compound is delivered at a concentration of between about 0.0001–30 mg/kg/day.

3. The method of claim 1 wherein the compound is delivered systemically at a concentration of about 0.01–10.0 mg/kg/day.

4. The method of claim 1 wherein the compound is delivered topically to the eye at a concentration of about 0.05–10.0 wt. %.

5. A method for treating uveitis, which comprises:
administering a therapeutically effective mount of a compound with the formula:

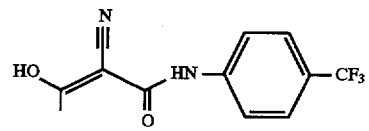

6. The method of claim 5 wherein the compound is delivered at a concentration of between about 0.0001–30 mg/kg/day.

7. The method of claim 5 wherein the compound is delivered systemically at a concentration of about 0.01–10.0 mg/kg/day.

8. The method of claim 5 wherein the compound is delivered topically to the eye at a concentration of about 0.05–10.0 wt. %.

* * * * *